United States Patent [19]

Duggan et al.

[11] Patent Number: 4,606,859

[45] Date of Patent: Aug. 19, 1986

[54] INFRA-RED ABSORBER

[75] Inventors: Peter J. Duggan, Manchester; Paul F. Gordon, Rochdale, both of England

[73] Assignee: Imperial Chemical Industries PLC, London, England

[21] Appl. No.: 714,673

[22] Filed: Mar. 21, 1985

[30] Foreign Application Priority Data

Mar. 21, 1984 [GB] United Kingdom ............... 8407303

[51] Int. Cl.$^4$ ............................................. C09B 47/04
[52] U.S. Cl. ................................... 540/122; 540/123; 540/124; 540/125; 540/127; 540/128; 540/130; 540/135; 540/136; 540/137; 540/139; 540/140
[58] Field of Search ............. 260/242.2, 245.1, 245.72, 260/245.73, 245.74, 245.76, 245.81, 245.82, 245.83, 245.85, 245.86

[56] References Cited

U.S. PATENT DOCUMENTS

| | | | |
|---|---|---|---|
| 2,290,906 | 7/1942 | Coffey et al. | 260/245.86 |
| 2,416,386 | 2/1947 | Haddock et al. | 260/245.72 |
| 2,456,274 | 12/1948 | Gutzwiller | 260/245.86 |
| 2,464,806 | 3/1949 | Haddock | 260/314.5 |
| 2,542,328 | 2/1951 | Haddock | 260/314.5 |
| 3,023,186 | 2/1962 | Geiger | 260/37 |
| 3,105,070 | 9/1963 | Bitterli | 260/245.72 X |
| 3,981,734 | 9/1976 | Cabut | 260/314.5 X |
| 4,002,642 | 1/1977 | Ische et al. | 260/314.5 |

FOREIGN PATENT DOCUMENTS

| | | |
|---|---|---|
| 1030959 | 5/1978 | Canada . |
| 1469766 | 1/1969 | Fed. Rep. of Germany . |
| A2455675 | 5/1975 | Fed. Rep. of Germany . |
| 2531823 | 2/1976 | Fed. Rep. of Germany . |
| 2439600 | 2/1976 | Fed. Rep. of Germany . |
| 2637861 | 3/1977 | Fed. Rep. of Germany . |
| 492177 | 10/1938 | United Kingdom . |
| 589118 | 6/1947 | United Kingdom . |
| 1164234 | 9/1969 | United Kingdom . |
| 1496256 | 12/1977 | United Kingdom . |

OTHER PUBLICATIONS

Chem. Abs., 89-112289v (Oksengendler), 1978.
Chem. Abs., 72-112801e (Arai), 1970.
Chem. Abs., 95-25024k (Derkacheva), 1981.
Chemistry of Synthetic Dyes (vol. V, 1971, pp. 241-282-Booth).
JCS (1983), pp. 1157-1163 (Barrett).
Lever, Advances in Inorganic Chemistry, vol. 7, pp. 27-33 (1965).

Primary Examiner—Richard L. Raymond
Attorney, Agent, or Firm—Cushman, Darby & Cushman

[57] ABSTRACT

An infra-red absorbing phthalocyanine compound in which each of at least five of the peripheral carbon atoms in the 1, 4, 5, 8, 9, 12, 13 or 16 positions (the "3,6-positions") of the phthalocyanine nucleus, as shown in Formula I, is linked by an atom from Group VB or Group VIB of the Periodic Table, other than oxygen, to a carbon atom of an organic radical. In preferred compounds each of the eight 3,6-positions is linked by an atoms from Group VB or Group VIB, especially sulphur, selenium or nitrogen, to an organic radical.

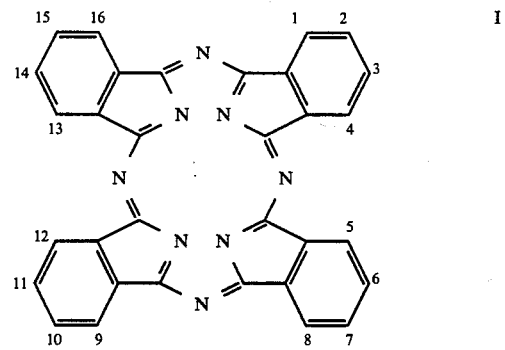

8 Claims, No Drawings

INFRA-RED ABSORBER

This specification describes an invention relating to certain poly(substituted)phthalocyanine compounds which absorb in the near infra-red region of the electromagnetic spectrum, e.g. from 750 to 1500 nm, and more especially from 750 to 1100 nm.

According to the present invention there is provided a phthalocyanine compound in which each of at least five of the peripheral carbon atoms in the 1, 4, 5, 8, 9, 12, 13 or 16 positions of the phthalocyanine nucleus, as shown in Formula I is linked by an atom from Group VB or Group VIB of the Periodic Table, other than oxygen, to a carbon atom of an organic radical.

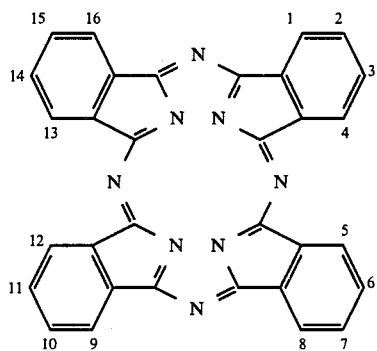

The carbon atoms in the 1, 4, 5, 8, 9, 12, 13, and 16 positions are hereinafter referred to as the "3,6-carbon atoms" by relation to the equivalent 3,6-positions in the four molecules of phthalic anhydride, see Formula II, from which the phthalocyanine can be derived.

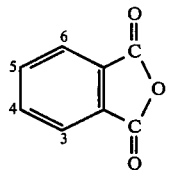

The remaining peripheral atoms of the phthalocyanine nucleus may be unsubstituted, i.e. carry hydrogen atoms, or be substituted by other groups, for example, halogen atoms or amino groups, or they may also be linked by an atom from Group VB or Group VIB of the Periodic Table to a carbon atom of an organic radical. It is preferred that each of at least six and, more preferably at least eight, of the 3,6 carbon atoms is linked by a Group VB or Group VIB atom to an organic radical.

In a first preferred class of phthalocyanine compound according to the present invention each of eight of the peripheral carbon atoms, at least five, preferably at least six and more preferably all, of which are 3,6 carbon atoms, is linked by an atom from Group VB or Group VIB to an organic radical. It is further preferred that each 3,6 carbon atom is linked to a separate organic radical. The remaining peripheral carbon atoms may carry other substituents, e.g. halogen atoms, but are preferably unsubstituted.

In a second preferred class each of from nine to sixteen of the peripheral carbon atoms, at least five, preferably at least six and more preferably eight, of which are 3,6 carbon atoms, is linked by an atom from Group VB or Group VIB to an organic radical. The remaining peripheral carbon atoms are preferably unsubstituted or carry halogen atoms. In the second class preferably each of at least ten, and more preferably at least twelve, of the peripheral carbon atoms is linked by a Group VB or Group VIB atom to an organic radical. Especially valuable compounds of this second class are those in which each of fifteen or sixteen of the peripheral carbon atoms is linked to an organic radical by an atom from Group VB or Group VIB.

Compounds of especial interest have an absorption peak above 750 nm, especially in the region from 750 to 1100 nm, and those of more especial interest have 90% of their absorption strength at or above 750 nm.

The organic radical may be an optionally substituted aliphatic, alicyclic or aromatic radical and is preferably an optionally substituted aromatic radical, especially from the benzene, naphthalene and mono- or bi-cyclic, heteroaromatic series. Examples of suitable aromatic radicals are optionally substituted phenyl, phenylene, naphthyl, especially naphth-2-yl, naphthylene, pyridyl, thiophenyl, furyl, pyrimidyl and benzthiazolyl. Aliphatic radicals are preferably from the alkyl and alkenyl series containing up to 20 carbon atoms, such as vinyl, allyl, butyl, nonyl, dodecyl, octadecyl and octadecenyl. Alicyclic radicals are preferably homocyclic containing from 4 to 8 carbon atoms, such as cyclohexyl. The organic radical may be monovalent and attached to a single peripheral carbon atom through a single Group VB or Group VIB atom or it may be polyvalent, preferably divalent, and attached to adjacent peripheral carbon atoms through identical or different atoms from Group VB and Group VIB. Where the organic radical is polyvalent it may be attached to two or more phthalocyanine nuclei.

Examples of substituents for the aromatic and heteroaromatic radicals are alkyl, alkenyl, alkoxy and alkylthio, and halo substituted derivatives thereof, especially those containing up to 20 carbon atoms, aryl, arylthio, especially phenyl and phenylthio, halogen, nitro, cyano, carboxyl, aralkyl, aryl- or alkyl-sulphonamido, aryl- or alkyl-sulphone, aryl- or alkyl-sulphoxide, hydroxy and primary, secondary or tertiary amino. Examples of substituents for the aliphatic and cycloaliphatic radicals are alkoxy, alkylthio, halo, cyano and aryl. In these substituents the alkyl and alkenyl groups preferably contain up to 20, and more preferably up to 4, carbon atoms and the aryl groups are preferably mono- or bi-homo- or hetero-cyclic. Specific examples of substituents are methyl, ethyl, dodecyl, methoxy, ethoxy, methylthio, allyl, trifluoromethyl, bromine, chlorine fluorine, benzyl, COOH, —COOCH$_3$, —COOCH$_2$C$_6$H$_5$, —NHSO$_2$CH$_3$, —SO$_2$C$_6$H$_5$, NH$_2$, —NHC$_2$H$_5$, and N(CH$_3$)$_2$.

Examples of suitable atoms from Group VB and Group VIB for linking the organic radical to a peripheral carbon atom of the phthalocyanine nucleus are sulphur, selenium, tellurium and nitrogen or any combination of these. Where an organic radical is linked to adjacent peripheral carbon atoms the second bridging atom may be any atoms from Group VB or Group VIB and examples are sulphur, oxygen, selenium, tellurium and nitrogen. Where the linking atom is nitrogen the free valency may be substituted or unsubstituted e.g. it may carry an alkyl group, preferably C$_{1-4}$-alkyl or an aryl group, preferably phenyl.

The phthalocyanine nucleus may be metal free, i.e. it may carry two hydrogen atoms at the centre of the nucleus, or it may be complexed with a metal or oxy-metal derivative, i.e. it may carry one or two metal atoms or oxy-metal groups complexed within the centre of the nucleus. Examples of suitable metals and oxy-metals are copper, lead, cobalt, nickel, iron, zinc, germanium, indium, magnesium, calcium, palladium, gallanyl and vanadyl.

Suitable compounds according to the first preferred class are those conforming to the following formula:

$$\text{octa-3,6-(RX)-Pc-M}_k \qquad \qquad \text{III}$$

wherein

M is a metal atom or hydrogen;
k is the inverse of half the valency of M;
Pc is the phthalocyanine nucleus;
X is sulphur, selenium, tellurium or NT where T is H, alkyl or aryl; and
R is a monovalent aromatic radical, preferably optionally substituted benzene or naphthalene; or
R and T together form an aliphatic or aromatic ring.

Throughout this specification the symbols, H$_2$Pc and MPc, in which M is a metal, e.g. Cu, Zn or Pb, will be used to indicate unmetallised and metallised phthalocyanines respectively.

Examples of compounds of the first preferred class and mostly conforming to Formula III are:

octa-3,6-(4-methylphenylthio)-CuPc
octa-3,6-(benzylthio)-CaPc
octa-3,6-(naphth-2-ylthio)-CuPc
octa-3,6-(4-methoxyphenylthio)-GePc
octa-3,6-(4-butoxyphenylthio)-CoPc
octa-3,6-(phenyltelluro)-H$_2$Pc
octa-3,6-(ethylthio)-NiPc
octa-3,6-(4-t-butylphenylthio)-(VO)-Pc
octa-3,6-(hexadecylthio)-CuPc
octa-3,6-(4-methylthiophenylthio)-CuPc
octa-3,6-(4-dodecyloxyphenylthio)-CuPc
hepta-3,6-(n-octylthio)-mono-3,6-chloro-CuPc
octa-3,6-(3,4-dimethylphenylthio)-H$_2$Pc
octa-3,6-(pyrid-2-ylthio)-H$_2$Pc
octa-3,6-(2,4-dimethoxyphenylthio)-CuPc
phen-1,4-ylenedithio-bis[hepta-3-6-(4-thiolphenylthio)]-CuPc
hepta-3,6-(4-butylphenylthio)-mono-3,6-chloro-H$_2$Pc
octapiperidino-octachloro-H$_2$Pc
octa(diethylamino)-H$_2$Pc
octa(ethylamino)-H$_2$Pc Suitable compounds from the second preferred class are those conforming to the following formulae:

$$M_k Pc(XR)_n(Y)_m \qquad \qquad \text{IV}$$

and $$M_k Pc(X^1\text{-}Q\text{-}X)_p(XR)_q(Y)_m \qquad \qquad \text{V}$$

wherein

M is a metal atom or hydrogen;
k is the inverse of half the valency of M;
Pc is the phthalocyanine mucleus;
X is sulphur, selenium, tellurium or NT where T is H, alkyl or aryl;
R is a monovalent aromatic radical; or
R and T together form an aliphatic or aromatic ring;
n is an integer from 10 to 16;
Y is a halogen atom;
m is an integer from 0 to 6;

X$^1$ is sulphur, selenium, tellurium, oxygen or NT in which T is H, alkyl or aryl
Q is a divalent aromatic radical;
p is an integer from 1 to 8;
q is an integer from 0 to 14;
provided that
(a) at least 6 of the groups represented by Q and R are attached through linking groups X to octa-3,6 carbon atoms, and
(b) n or the sum of 2p and q is from 10 to 16, preferably from 12 to 16 and more preferably 15 or 16.

Examples of compounds conforming to Formulae IV and V are:

deca(4-methylphenylthio)-pentachloro-CuPc
deca(4-t-butylphenylthio)-pentachloro-CuPc
deca(naphth-2-ylthio)-hexachloro-CuPc
deca(4-ethylthiophenylthio)-pentachloro-CuPc
unadeca(4-methylphenylthio)-bromo-CuPc
unadeca(4-dimethylaminophenylthio)-pentachloro-CuPc
dodeca(4-methylphenylthio)-CuPc
dodeca(4-t-butylphenylthio)-trichloro-CuPc
terdeca(4-butoxyphenylthio)-dichloro-InPc
pentadeca(n-butylthio)-CuPc
pentadeca(4-carboxylphenylthio)-CuPc
pentadeca(4-t-butylphenylthio)-CuPc
pentadeca(phenylseleno)CuPc
pentadeca(naphth-2-ylthio)-MgPc
pentadeca(naphth-1-ylthio)-CuPc
pentadeca(4-methoxyphenylthio)-CuPc
pentadeca(4-dodecyloxyphenylthio)-CuPc
pentadeca(4-methylthiophenylthio)-CuPc
pentadeca(phenylthio)-CuPc
pentadeca(4-butoxyphenylthio)-CuPc
pentadeca(n-dodecylthio)-CuPc
pentadeca(benzimidazol-2-ylthio)-CuPc
hexadeca(4-methylphenylthio)-CuPc
hexadeca(4-methylphenylthio)-ZnPc
hexadeca-anilino-H$_2$Pc
hexadeca(4-methylphenylthio)-PbPc
hexadeca(4-methylphenylthio)-H$_2$Pc
hexadeca(4-chlorophenylthio)-NiPc
hexadeca(piperidino)-H$_2$Pc
hepta(4-methylphen-1,2-ylenedithio)-di(4-methyl-2-thiolphenylthio)-CuPc
hepta(4-methylphen-1,2-ylenedithio)-di(4-methyl-2-thiolphenylthio)-H$_2$Pc
octa(phen-1,2-ylenediamino)H$_2$Pc
hexadeca(diethylamino)H$_2$Pc
hexadeca(ethylamino)H$_2$Pc Preferred values for, and examples of, the groups represented by R, Q and T are as given hereinbefore in respect of the organic radical. Where R and T together form an aliphatic or aromatic ring this may be, for example, pyrid-1-yl, pyrimid-1-yl, piperidin-1-yl, morpholin-1-yl, pyrrol-1-yl or pyrrolidin-1-yl.

The phthalocyanine compounds of the present invention can be prepared by heating a phthalocyanine compound carrying halogen atoms attached to the preripheral carbon atoms to which it is wished attach the Group VB or Group VIB atoms with at least six equivalents of an organic thiol, or an equivalent compound in which the sulphur in the thiol group is replaced by selenium (selenol), tellurium (tellurol) or NT (amine), in an organic solvent.

The compounds of the first preferred class in which X is sulphur can be prepared by heating an octa-halophthalocyanine, in which at least six, and more preferably all, of the halogen atoms are attached to 3,6 carbon atoms, with at least eight equivalents of an organic thiol in an organic solvent, The compounds of the second preferred class in which X is sulphur can be prepared by heating a phthalocyanine carrying at least nine halogen atoms, at least six of which are attached to 3,6 carbon atoms, with at least nine equivalents of an organic thiol in an organic solvent. If the organic thiol also carries another substituent, such as a second thiol group or a hydroxy or a primary or secondary amino group, which will react with a halogen atom attached to an adjacent peripheral carbon atom on the phthalocyanine nucleus, the organic radical of the thiol may become linked to two adjacent peripheral carbon atoms.

Other compounds of the preferred classes may be prepared by using, in place of the thiol, an equivalent compound in which the sulphur is replaced by selenium, tellurium or a group, NT.

The organic solvent, which need not necessarily be a liquid at ambient temperatures and may only partially dissolve the reactants, preferably has a boiling point from 100° C. to 300° C. and more preferably from 150° C. to 250° C. The organic solvent is preferably essentially inert although it may catalyse the reaction. Examples of suitable solvents are methylcyclohexanol, octanol, ethylene glycol, and especially benzyl alcohol and quinoline.

Reaction is conveniently carried out under reflux, preferably from 100° C. to 250° C. and more preferably above 150° C., in the presence of an acid binding agent, such as potassium or sodium hydroxide or sodium carbonate, to neutralise the halo acid formed. The product may be isolated by filtration or by distillation of the organic liquid. The isolated product is preferably purified by repeated recrystallisation from a suitable solvent, such as ethanol, chloroform or pyridine, and/or chromatography, using a silica-filled column and an aromatic solvent, such as toluene or xylene, as eluent.

The phthalocyanine compounds of the present invention can also be prepared by heating an o-phthalic acid derivative, especially o-phthalonitrile (o-PN), carrying substituted-thio, seleno, telluro or NT groups in the 3 and 6 positions. The process may also include an unsubstituted o-PN or an o-PN carrying substituents in other than the 3 and 6 positions, provided the proportion of the o-PN carrying substituted-thio etc groups is sufficient to ensure that there are at least five substituted-thio etc, groups in the phthalocyanine product. The process is conveniently performed in a solvent in the presence of a base. It may also be promoted by the addition of a catalyst, such as ammonium molybdate.

This process is analogous to the known method for preparing unsubstituted phthalocyanines from ortho-phthalic acid derivatives such as those described in Journal of the Chemical Society, (1938), pp 1157–63; Advances in Inorganic Chemistry (Radiochemistry), (1965), 7, p 27 & Chemistry of Synthetic Dyes, (1971), 5, pp 241–82.

The solvent preferably has a boiling point from 50° C. to 300° C., more preferably from 70° C. to 200° C. and need not be a liquid at ambient temperatures or completely dissolve the reactants. It is preferably essentially inert though it may interact with the base, catalyse the reaction or even partially replace the substituted-thio groups in the phthalocyanine compound. Preferred solvents are aliphatic alcohols such as iso-amyl alcohol, octanol and benzyl alcohol.

Where an alcohol is employed as solvent it is possible for one or more alcohol residues to replace the substituted thio, etc. groups attached to the o-PN and become attached to a peripheral carbon atom of the phthalocyanine through an oxygen atoms. Such a phthalocyanine, carrying one or more organic radicals attached through oxygen atoms, provided it also carries at least five organic radicals each of which is attached through a Group VB or Group VIB atom other than oxygen, is a further feature of the present invention.

The reaction is conveniently carried out between 100° C. and 150° C. or under reflux in the presence of a base, such as an alkoxide formed between an alkali metal and an alcohol, preferably an aliphatic alcohol. A particularly suitable base is lithium iso-amyl oxide because lithium phthalocyanines are generally soluble in alcohols.

Different metals may be introduced into the phthalocyanine by heating the o-PN with a suitable salt of the appropriate metal or heating lithium phthalocyanine with a solvent compound of the appropriate metal. A metal-free phthalocyanine may be obtained by acidification of the lithium phthalocyanine, in some cases by merely contacting it with an acidic material, such as a silica-gel, or by heating it with a stronger acid, such as p-toluene-sulphonic acid.

The phthalocyanine compound in accordance with the present invention is useful for absorbing electromagnetic energy from an infra-red source and optionally making it available as heat energy. Particular applications where this property can be utilised for practical effect are infra-red inks, liquid crystal displays, infra-red protection systems, such as welding goggles, sun visors, vehicle windscreens and infra-red security systems, e.g. computer-controlled locks and alarms. The position of the absorption maximum depends upon the nature of the compound and the substrate on or in which it is incorporated. Many of the compounds of the present invention exhibit a bathochromic shift of up to 50 m$\mu$m when deposited on glass compared with a solution in an organic liquid.

A liquid crystal cell, for the formation of latent images, can be rendered laser-addressable by dissolving a compound in accordance with the present invention in the liquid crystal medium. For example, Pentadeca(naphth-2-ylthio)-CuPc has an absorption maximum at 782 m$\mu$m and a solubility of 0.5% in the liquid crystal material E7, which is available from BDH Chemicals, of Poole in Dorset, England, and Hepta(4-methylphen-1,2-ylenedithio)-di(4-methyl-2-thiolphenylthio)-CuPc has an absorption maximum at 820 m$\mu$m and a solubility of 0.3% in the liquid crystal material, E7.

A security card can be rendered opaque to infra-red irradiation by the application to a predetermined area of an ink containing the present compound, for example, by thermal transfer or ink-jet printing. In this way a unique pattern, recognisable by a programmed detector, can be applied to the security card. By suitable choice of compound, a composite pattern absorbing at one or more wavelengths can be formed. For example, Octa-3,6-(2-aminophenylthio)CuPc has an absorption maximum at 950 m$\mu$m Octa-3,6-(4-methoxyphenylthio)-CuPc has an absorption maximum at 805 m$\mu$m and Pentadeca-(4-methylphenylthio)-CuPc has an absorption maximum at 775 m$\mu$m.

The invention is further illustrated by the following examples in which all parts and percentages are by weight unless otherwise indicated.

EXAMPLE 1

A mixture of 3.06 g of 4-methylphenylthiol, 1.26 g of KOH and 10 ml of quinoline was stirred at 130°–140° C. for 60 minutes and 5.69 g of octa-3,6-chloro-$H_2$Pc was added. The mixture was then stirred at 180° C. for 1 hour and at 200°–210° C. for 30 minutes. The mixture was then cooled to 100° C. and diluted with 50 ml of ethanol (74 OP). After cooling to 25° C. the solid was filtered and dissolved in toluene. The toluene solution was passed through a silica column using toluene as eluent and the main fraction collected and isolated by evaporation to yield 0.26 g of dry octa-3,6-(4-methylphenylthio)-$H_2$Pc.

EXAMPLE 2

A mixture of 6.29 g of 4-methylphenylthiol, 3.29 g of KOH and 20 ml of quinoline was stirred at 130°–160° C. for 90 minutes and 4.16 g of octa-3,6-chloro-CuPc was added. The mixture was then stirred at 180°–200° C. for 5.5 hour, cooled to 80° C. and diluted with 50 ml of ethanol (74 OP). After cooling to 25° C. the solid was filtered, washed with ethanol and dissolved in toluene. The toluene solution was passed through a silica column using toluene as eluent and the main fraction collected and isolated by evaporation to yield dry octa-3,6-(4-methylthio)-CuPc.

EXAMPLES 3 TO 17

Further compounds within the scope of the present invention in accordance with Formula III were prepared by the methods of Examples 1 and 2, using equimolar quantities of appropriate thiols in place of the thiols described in the Examples, as set out in Table 1. In each product containing less than eight substituted thio groups, the free 3,6-positions are occupied by chloro groups.

The octa-3,6-Pcs used in Examples 1 to 17 were made from purified dichlorophthalic anhydride comprising >85% of the 3,6-dichloro isomer. The dichlorophthalic anhydride was purified by by centrifugal distillation or fractional crystallisation.

EXAMPLE 18

A mixture of 12.4 g of 4-methylphenylthiol, 5.6 g of KOH and 20 ml of quinoline was stirred at 140° C. for 60 minutes and 5.69 g of tetradecachloromonobromo-CuPc was added. The mixture was then stirred vigorously at 160°–180° C. for 1 hour, cooled to 100° C. and diluted with 50 ml of ethanol (74 OP). After cooling to ambient the solid was filtered, washed with ethanol, water and ethanol and dried to give 7.8 g crude material. The crude material was passed through a silica column using toluene as eluent and the main fraction collected and isolated by evaporation to yield 5.77 g of dry pentadeca(4-methylthio)-CuPc.

EXAMPLE 19

A mixture of 1.65 g of 4-methylphenylthiol, 0.83 g of KOH and 10 ml of quinoline was stirred at 140° C. for 30 minutes and 2.8 g of tetradecachloro-monobromo-CuPc was added. The mixture was then stirred at 180°–200° C. for 5 hours, cooled to 80° C. and diluted with 30 ml of ethanol (74 OP). After cooling to 30° C. the solid was filtered, washed with ethanol and dried to give 3.6 g crude material. The crude material was passed through a silica column using toluene as eluent and the main fraction collected and isolated by evaporation to yield 0.92 g of dry deca(4-methylthio)-pentachloro-CuPc.

EXAMPLES 20 TO 36

Further compounds within the scope of the present invention in accordance with Formula IV were prepared by the methods of Examples 18 and 19, using equimolar quantities of appropriate thiols or selenols in place of the thiols described in the Examples, as set out in Table 2. In each product having less than fifteen substituted thio groups, the free positions are occupied by chloro groups.

TABLE 1

| Ex | Method | Thiol | Product |
|---|---|---|---|
| 3 | Ex 1 | 3-methylphenyl | octa-3,6(3-methylphenylthio)$H_2$Pc |
| 4 | Ex 1 | 4-t-butylphenyl | hepta-3,6(4-t-butylphenylthio)$H_2$Pc |
| 5 | Ex 1 | 4-t-butylphenyl | octa-3,6(4-t-butylphenylthio)$H_2$Pc |
| 6 | Ex 2 | 4-t-butylphenyl | octa-3,6(4-t-butylphenylthio)CuPc |
| 7 | Ex 1 | 4-n-nonylphenyl | hepta-3,6(4-n-nonylphenylthio)$H_2$Pc |
| 8 | Ex 1 | 4-dodecylphenyl | hepta-3,6(4-dodecylphenylthio)$H_2$Pc |
| 9 | Ex 1 | 3,4-dimethylphenyl | hexa-3,6(3,4-dimethylphenylthio)$H_2$Pc |
| 10 | Ex 1 | 4-methoxyphenyl | octa-3,6(4-methoxyphenylthio)$H_2$Pc |
| 11 | Ex 2 | 4-methoxyphenyl | octa-3,6(4-methoxyphenylthio)CuPc |
| 12 | Ex 2 | 4-butoxyphenyl | octa-3,6(4-butoxyphenylthio)CuPc |
| 13 | Ex 1 | 4-dodecyloxyphenyl | octa-3,6(4-dodecyloxyphenylthio)$H_2$Pc |
| 14 | Ex 2 | 4-dodecyloxyphenyl | octa-3,6(4-dodecyloxyphenylthio)CuPc |
| 15 | Ex 2 | naphth-2-yl | octa-3,6(naphth-2-ylthio)CuPc |
| 16 | Ex 1 | 4-octoxyphenyl | octa-3,6(4-octoxyphenylthio)$H_2$Pc |
| 17 | Ex 2 | 4-octoxyphenyl | penta-3,6(4-octoxyphenylthio)CuPc |

TABLE 2

| Example | Thiol/Selenol | Product |
|---|---|---|
| 20 | t-butylphenyl | pentadeca(t-butylphenylthio)CuPc |
| 21 | 3-methylphenyl | pentadeca(3-methylphenylthio)CuPc |
| 22 | 4-methoxyphenyl | pentadeca(4-methoxyphenylthio)CuPc |
| 23 | 4-butyoxyphenyl | terdeca(4-butoxyphenylthio)CuPc |
| 24 | 4-butoxyphenyl | pentadeca(4-butoxyphenylthio)CuPc |
| 25 | 4-dodecoxyphenyl | pentadeca(4-dodecoxyphenylthio)CuPc |
| 26 | phenyl | pentadeca(phenylthio)CuPc |
| 27 | 2-methoxyphenyl | tetradeca(2-methoxyphenylthio)CuPc |

TABLE 2-continued

| Example | Thiol/Selenol | Product |
|---|---|---|
| 28 | 4-methylthiophenyl | pentadeca(4-methylthiophenylthio)CuPc |
| 29 | 4-ethylthiophenyl | deca(4-ethylthiophenylthio)CuPc |
| 30 | 4-chlorophenyl | pentadeca(4-chlorophenylthio)CuPc |
| 31 | 4-(dimethylamino)phenyl | unadeca(4-dimethylaminophenylthio)CuPc |
| 32 | naphth-1-yl | terdeca(naphth-1-ylthio)CuPc |
| 33 | naphth-2-yl | pentadeca(naphth-2-ylthio)CuPc |
| 34 | phenylselenol | pentadeca(phenylseleno)CuPc |

EXAMPLE 35

A mixture of 7.75 g of 4-methylphenylthiol, 3.36 g of KOH, and 10 ml of quinoline was stirred at 130° C. for 30 minutes and 3.18 g of hexadecachloro-PbPc was added. The mixture was then stirred at 180°-190° C. for 30 minutes, cooled to 50° C. and diluted with 30 ml of toluene. The crude material was passed through a silica gel column using toluene as eluent and the main fraction collected. This was isolated by evaporation to give 0.45 g of hexadeca(4-methylphenylthio)PbPc.

EXAMPLES 36 TO 40

Further compounds within the scope of the present invention in accordance with Formula IV were prepared by the method of Example 35 using equimolar quantities of appropriate thiols in place of the 4-methylphenylthiol and equimolar quantities of an appropriate hexadecachloro-Pc in place of the hexadecachloro-PbPc, as set out in Table 3. In each product having less than sixteen substituted thio groups, the free positions are occupied by chloro groups.

TABLE 3

| Example | Thiol | Product |
|---|---|---|
| 36 | 4-methylphenyl | hexadeca(4-methylphenylthio)H$_2$Pc |
| 37 | 4-methylphenyl | hexadeca(4-methylphenylthio)CuPc |
| 38 | 4-methylphenyl | hexadeca(4-methylphenylthio)ZnPc |
| 39 | 4-chlorophenyl | hexadeca(4-chlorophenylthio)CuPc |
| 40 | naphth-2-yl | deca(naphth-2-ylthio)H$_2$Pc |

EXAMPLE 41

A mixture of 3.12 g of 4-methylphen-1,2-ylenedithiol, 2.24 g of KOH and 10 ml of quinoline was stirred at 30° C. for 30 minutes and 2.13 g of hexadecachloro-H$_2$Pc was added. The mixture was then stirred at 80° C. for 1 hour, 100° C. for 1 hour and 130° C. for 1 hour. It was then cooled to 80° C. and diluted with 100 ml of ethanol (74 OP). After cooling to 25° C. the solid was filtered, washed twice with ethanol and dried. The crude material was passed through a silica column using chloroform as eluent. The main fraction collected, isolated by evaporation and recrystallised from toluene/ether to yield 2.00 g of hepta(4-methylphen-1,2-ylenedithio)-di(4-methyl-2-thiolphenylthio)-H$_2$Pc.

EXAMPLES 42 AND 43

Further compounds within the scope of the present invention in accordance with Formula V were prepared by the method of Example 42 using equimolar quantities of the appropriate aminothiol in place of the 4-methylphen-1,2-ylenedithiol and/or tetradecachloromonobromo-CuPc in place of the hexadecachloro-H$_2$Pc, as set out in Table 4.

TABLE 4

| Example | Thiol | Product |
|---|---|---|
| 42 | 4-methylphen-1,2-ylene dithiol | hepta(4-methylphen-1,2-dithio-ylene)-mono(4-methyl-2-thiolphenylthio)-CuPc |
| 43 | 2-aminophenylthiol | penta(phen-1-amino-2-thio-ylene)-penta(2-aminophenylthio)-CuPc |

EXAMPLE 44

A mixture of 7.36 g of tetra(ethylthio)-o-PN and lithium alkoxide (comprising 0.0525 g of lithium in 21 ml of isoamyl alcohol was stirred at 120°-130° C. for 2 hours and 130°-135° C. for a further 1 hour. After cooling to 50° C., 100 ml of methanol was added and the mixture cooled to 20° C. The precipitate which formed was filtered and washed well with methanol before being dissolved in toluene. The toluene solution was passed through a silica column using toluene as eluent. The main fraction was collected and isolated by evaporation to give pentadeca(ethylthio)-monoisoamyloxy-H$_2$Pc.

EXAMPLE 45

A mixture of 3.83 g of tetra(cyclohexylthio)-o-PN and lithium alkoxide (0.023 g of lithium in 7.5 ml of iso-amyl alcohol) was stirred at 120°-30° C. for 2½ hours. After cooling to 25° C., a solution of 1.79 g of zinc chloride in 25 ml of anhydrous methanol was added. The mixture was then stirred at 25° C. for 1 hour and at 120°-30° C. for 30 minutes. After cooling to 20° C., the precipitate was filtered off and washed with methanol before being dissolved in toluene. The toluene solution was passed through a silica column, using toluene as eluent and the main fraction collected. The product was isolated by evaporation to give hexadeca(cyclohexylthio)-ZnPc.

EXAMPLES 46 TO 65

Further compounds within the scope of the present invention in accordance with Formula III or Formula IV were prepared by the methods of Examples 44 and 45 using equimolar quantities of appropriate di- or tetra-(substituted-thio)-o-PN in place of the tetra(ethylthio)-o-PN of Example 44 and the tetra(cyclohexylthio)-o-PN of Examples 45 and, where appropriate, a metal chloride, as set out in Table 5.

TABLE 5

| Example | Subs-o-PN | Product |
|---|---|---|
| | As in Example 45 (with di- or tetra-(substituted-thio)-o-PN) | |
| 46 | tetraethyl | tetradeca(ethylthio)monoamyloxy-H$_2$Pc |
| 47 | tetraethyl | (ethylthio)$_{15.3}$(amyloxy)$_{0.7}$-H$_2$Pc |
| 48 | tetra-n-propyl | hexadeca(n-propylthio)-H$_2$Pc |

TABLE 5-continued

| Example | Subs-o-PN | Product |
|---|---|---|
| 49 | tetra-i-propyl | pentadeca(i-propylthio)monoamyloxy-$H_2Pc$ |
| 50 | tetra-n-butyl | pentadeca(n-butylthio)monoamyloxy-$H_2Pc$ |
| 51 | tetra-n-pentyl | pentadeca(n-pentylthio)monoamyloxy-$H_2Pc$ |
| 52 | tetraethyl/tetrabutyl | octa(butylthio)octa(ethylthio)-$H_2Pc$ |
| 53 | tetra(ethyl/butyl) (random) | octa(butylthio)octa(ethylthio)-$H_2Pc$ |
| 54 | tetracyclohexyl | pentadeca(cyclohexylthio)monoamyloxy-$H_2Pc$ |
| 55 | tetra-n-octyl | hexadeca(n-octylthio)-$H_2Pc$ |
| 56 | tetra-s-butyl | pentadeca(s-butylthio)monoamyloxy-$H_2Pc$ |
| 57 | tetrabenzyl | pentadeca(benzylthio)monoamyloxy-$H_2Pc$ |
| 58 | tetraphenyl | hexadeca(phenylthio)-$H_2Pc$ |
| 59 | 3,6-di(iso-propyl) | octa-3,6-(isopropylthio)-$H_2Pc$ |
| As in Example 46 (with tetra(substituted-thio)-o-PN & $CuCl_2$) | | |
| 60 | tetra-n-propyl | pentadeca(n-propylthio)monoamyloxy-CuPc |
| 61 | tetra-n-pentyl | pentadeca(n-pentylthio)monoamyloxy-CuPc |
| 62 | tetracyclohexyl | pentadeca(cyclohexylthio)monoamyloxy-CuPc |
| 63 | tetra-s-butyl | pentadeca-s-butylthio)monoaryloxy-CuPc |
| 64 | tetrabenzyl | pentadeca(benzylthio)monoaryloxy-CuPc |
| As in Example 46 (with tetra(substituted-thio)-o-PN & $PbCl_2$ | | |
| 65 | tetracyclohexyl | pentadeca(cyclohexylthio)monoamyloxy-PbPc |

EXAMPLE 66

A mixture of 0.46 g of dipiperidino-dichloro-o-PN and lithium alkoxide (comprising 0.007 g of lithium and 5 ml of isoamyl alcohol) was stirred at 120°–130° C. for 20 minutes. After cooling to 20° C., 10 ml of chloroform was added and the mixture passed through a silica column using chloroform as eluent. A fraction was collected and isolated by evaporation to give octapiperidino-octachloro-$H_2Pc$.

The dipiperidino-dichloro-o-PN was prepared by reacting piperidine with tetra-chloro-o-PN in dimethylformamide and potassium carbonate using the method described in UK 1,489,394.

In all the above preparations structures were confirmed by elemental analysis and the products were characterised by the determination of melting points, absorption maxima and/or extinction coefficients.

PROPERTIES OF INFRA-RED ABSORBERS

The products of the Examples have the properties set out in Table 6. Absorption maxima were measured as solutions in chloroform (Chlor), toluene (Tol) of after deposition on glass (Glass) unless otherwise indicated. Extinction coefficients were determined in toluene or the only solvent in which the absorption maximum was recorded.

TABLE 6

| Example | Absorption Maxima (mμm) | | | Extinction Coefficient | Melting Point (°C.) |
|---|---|---|---|---|---|
| | Chlor | Tol | Glass | | |
| 1 | 813 | 805 | 828 | 170,000 | >200 |
| 2 | 797 | 787 | 797 | 156,000 | >200 |
| 3 | 805 | 797 | 818 | 160,000 | >250 |
| 4 | 798 | 790 | | 173,000 | >250 |
| 5 | 793 | | 797 | 152,000 | >250 |
| 6 | 803 | | 797 | 216,000 | >280 |
| 7 | 800 | | 809 | | 75 |
| 8 | 789 | 787 | 795 | | 70 |
| 9 | 807 | 803 | 830 | | >200 |
| 10 | 799 | 792 | | 161,500 | |
| 11 | 805 | | 813 | 155,000 | |
| 12 | 800 | 786 | | | |
| 13 | 818 | 808 | 859 | | 95 |
| 14 | 807 | 794 | 822 | | <70 |
| 15 | 799 | | 796 | 136,000 | |
| 16 | 816 | 806 | 846 | | 75 |
| 17 | 775 | | | | |
| 18 | 775 | 768 | 790 | 169,000 | 120 |
| 19 | 758 | 752 | 770 | 174,000 | 148 |
| 20 | 774 | 760 | 784 | 142,000 | 128 |
| 21 | 771 | 766 | 786 | | 95 |
| 22 | 786 | | 801 | 190,000 | |
| 23 | 775 | 768 | 797 | 158,000 | 140 |
| 24 | 786 | 780 | 801 | 182,000 | 100 |
| 25 | 778 | 770 | 792 | 162,000 | 120 |
| 26 | 772 | 768 | 794 | | |
| 27 | 770 | | | | |
| 28 | 788 | 784 | 810 | 208,500 | 168 |
| 29 | 756 | 752 | | | |
| 30 | 774 | | 787 | 181,000 | 169 |
| 31 | 782 | | 805 | 118,000 | >200 |
| 32 | 765 | 760 | | | |
| 33 | 786 | 781 | 799 | 197,000 | 143 |
| 34 | 776 | | | | |
| 35 | 769 | | 792 | | 223 |
| 36 | 769 | | | | |
| 37 | 778 | 770 | 796 | 220,000 | 142 |
| 38 | 768 | | 791 | | 160 |
| 39 | 770 | | 789 | 220,000 | |
| 40 | 744 | | | | |
| 41 | 800 | 797 | 832 | 94,000 | >200 |
| 42 | 790 | 787 | 828 | 91,000 | >200 |
| 43 | 909 (in Pyridine) | | | | |
| 44 | 804 | 807 | 827 | | >250 |
| 45 | 846 | 852 | 860 | 95,000 | 145–150 |
| 46 | 801 | 802 | | | >250 |
| 47 | 805 | 808 | 830 | 149,000 | >250 |
| 48 | 802 | 800 | 819 | 157,600 | 230 |
| 49 | 809 | | 823 | 136,500 | 250 |
| 50 | 807 | | 817 | 147,000 | 95/35 |
| 51 | 802 | 802 | | 162,500 | <30 |
| 52 | 809 | 805 | 815 | 129,000 | <30 |
| 53 | 803 | 797 | 815 | 115,500 | <30 |
| 54 | 812 | 810 | 818 | 120,000 | 289 |
| 55 | 818 | 811 | | | <30 |
| 56 | 805 | 801 | | 133,000 | 260–280 |
| 57 | 810 | 809 | | 84,000 | 100–180 |
| 58 | 790 | | | | |
| 59 | 802 | | | 167,000 | |
| 60 | 783 | 785 | 805 | 170,500 | 260 |
| 61 | 784 | 783 | | 182,000 | <30 |
| 62 | 789 | 781 | 803 | 163,000 | 286 |
| 63 | 787 | 778 | | 168,000 | 270–280 |
| 64 | 797 | 789 | | 109,000 | 100–200 |
| 65 | 838 | 830 | 840 | 111,000 | 175–230 |
| 66 | 835 | | | | |

We claim:

1. A phthalocyanine compound in which each of five of the peripheral carbon atoms in the 1, 4, 5, 8, 9, 12, 13 and 16 positions of the phthalocyanine nucleus, as shown in the following formula:

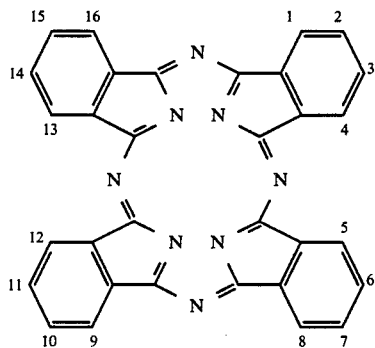

is linked by a sulphur, selenium, tellurium or nitrogen atom to a carbon atom of an organic radical selected from alkyl, alkenyl, $C_{4-8}$-cycloalkyl, unsubstituted or substituted by a group selected from alkoxy, alkylthio, halogen, cyano and aryl; or selected from phenyl, phenylene, naphthyl, naphthylene and mono or bicyclic heteroaryl which are unsubstituted or substituted by a group selected from alkyl, alkoxy and alkylthio and halogen substituents thereof, phenyl, phenylthio, halogen, nitro, cyano, carboxyl, aralkyl, aryl- and alkyl-sulphonamido, aryl- and alkyl-sulphone, aryl and alkyl-sulphoxide, hydroxy and primary, secondary and tertiary amino, in which all alkyl groups contain up to 20 carbon atoms and all aryl groups are mono- or bi-homo- or hetero-cyclic.

2. A phthalocyanine compound according to claim 1 wherein each of the eight peripheral carbon atoms in the 1, 4, 5, 8, 9, 12, 13 and 16 positions of the phthalocyanine nucleus is linked by a sulphur, selenium, tellurium or nitrogen atom to a carbon atom of the organic radical.

3. A phthalocyanine compound according to claim 2 wherein the remaining peripheral carbon atoms of the phthalocyanine nucleus are unsubstituted.

4. A phthalocyanine compound according to claim 1 or claim 2 wherein each of from one to eight of the remaining peripheral carbon atoms of the phthalocyanine nucleus is linked by a sulphur, selenium, tellurium or nitrogen atom to a carbon atom of the organic radical.

5. A phthalocyanine compound according to any one of claims 2 and 1 wherein each of fifteen or sixteen of the peripheral carbon atoms of the phthalocyanine nucleus is linked by a sulphur, selenium, tellurium or nitrogen atom to a carbon atom of the organic radical.

6. A phthalocyanine compound according to any one of claims 2, 3 and 1 having an absorption maximum above 750 m$\mu$m.

7. A phthalocyanine compound according to any one of claims 2, 3 and 1 wherein the organic radical is bivalent and attached to adjacent peripheral carbon atoms on the phthalocyanine nucleus through a second bridging atom selected from sulphur, oxygen, selenium, tellurium and nitrogen.

8. A phthalocyanine compound according to claim 4 wherein at least one of the peripheral carbon atoms of the phthalocyanine nucleus is linked to the organic radical through an oxygen atom.

* * * * *